United States Patent [19]

Oliver

[11] Patent Number: 5,043,706

[45] Date of Patent: Aug. 27, 1991

[54] SYSTEM AND METHOD FOR DETECTING BUBBLES IN A FLOWING FLUID

[75] Inventor: James A. Oliver, Webster, N.Y.

[73] Assignee: Eastman Kodak Company, Rochester, N.Y.

[21] Appl. No.: 600,459

[22] Filed: Oct. 19, 1990

[51] Int. Cl.$^5$ ............................................. G08B 21/00
[52] U.S. Cl. ...................................... 340/603; 340/627; 340/632; 73/19.03; 73/19.1
[58] Field of Search ....................... 340/603, 632, 627; 73/19.03, 19.04, 19.1, 19.11; 604/65, 122; 128/661.09, 662.01

[56] References Cited

U.S. PATENT DOCUMENTS

| | | | |
|---|---|---|---|
| 3,269,172 | 8/1966 | McGaughey | 73/614 X |
| 3,403,554 | 10/1968 | Chevalier et al. | 73/861.41 |
| 4,083,225 | 4/1978 | Day et al. | 73/19.03 |
| 4,112,735 | 9/1978 | McKnight | 73/19.03 |
| 4,112,773 | 9/1978 | Abts | 73/19.1 X |
| 4,122,713 | 10/1978 | Stasz et al. | 73/19.1 X |
| 4,130,010 | 12/1978 | Wonn | 73/19.03 |

Primary Examiner—Joseph A. Orsino
Assistant Examiner—Jeffery A. Hofsass
Attorney, Agent, or Firm—Francis H. Boos, Jr.

[57] ABSTRACT

Reliability of bubble or particle detection in a flowing fluid is improved using a pulsed doppler frequency detector. When an echo signal is received, impliedly indicating the existence of a bubble or particle in the carrier fluid, then, based on the flow rate of the carrier fluid, a predetermined time interval is established following a second interrogating pulse during which the second interrogating pulse would be predicted to produce an echo if the first echo did, in fact, represent a real bubble or particle in the fluid. Detection of the second echo during this time interval confirms the existence of the bubble or particle. For fluid flows with cross section velocity profiles that are not constant, e.g. laminar flow, a plurality of different predicted time intervals are established for different points in the velocity profile spaced radially from the fluid conduit and multiple sensing cycles are employed to thereby detect bubbles or particles at different radial positions in the fluid cross section.

6 Claims, 2 Drawing Sheets

SYSTEM AND METHOD FOR DETECTING BUBBLES IN A FLOWING FLUID

FIELD OF INVENTION

This invention relates to the field of bubble detection in moving fluids and more particularly to apparatus and methods for detecting the presence of moving bubbles or the like with a higher degree of reliability than heretofore.

BACKGROUND OF INVENTION

The need to reliably detect bubbles in a moving fluid can be important in many situations. For example, in film coating operations, bubbles existing in the film emulsion at the coating stage can cause streaking in the resultant film coating with consequent loss of film production. Since the detection of bubbles can result in corrective action such as marking of suspected defect areas on film webs for later excission or that otherwise results in temporary interruption of the coating process, it is important that bubble detection operate reliably and not give false readings of bubble detection when, in fact, no bubbles are present in the fluid.

One well known bubble detection technique utilizes doppler frequency shift detection to detect the existence of a moving bubble in the fluid. A transducer is used to transmit and receive bursts of high frequency energy along the length of a conduit in which the fluid is flowing. Reflected echoes received by the transducer are analyzed to find any with characteristic frequency shifts that would indicate the presence of bubbles in the fluid. It will be appreciated that such detection techniques will also detect moving solid particles and reference to bubbles herein should be understood to encompass solid particles as well.

While generally useful for this purpose, it has been found that such systems have detection reliability problems in which there is uncertainty as to whether the detection is indicative of a real event, i.e. a moving bubble or is just a false detection indication due to electrical or mechanically induced noise in the signal.

It is therefore an object of the invention to provide apparatus and methods for detection of bubbles in a moving fluid which provides improved reliability of detection.

SUMMARY OF INVENTION

In accordance with the invention, therefore, there is provided an improved method for sensing the existence of bubbles in a fluid flowing through a section of an elongated conduit by means of acoustic echo sensing, wherein the improvement comprises the steps of sensing the velocity of the fluid flowing in the conduit section, transmitting a first burst of acoustic energy along the conduit section and detecting a doppler frequency shifted echo signal implicitly indicating the existence of a bubble moving in the conduit section. The method of the invention further comprises the steps of establishing, on the basis of the fluid velocity, a predetermined time interval during which an echo signal would occur from a second burst of acoustic energy transmitted a known time after the first transmitted burst if the implicit existence of the bubble is, in fact, real; transmitting the second burst at the known time after the first burst, detecting echo signals from the second transmitted burst and establishing the real existence of the bubble only if an echo signal is detected during the predetermined time interval.

In accordance with another feature of the invention, apparatus for detecting foreign bodies such as bubbles in a moving fluid comprises a section of conduit adapted to flow fluid therethrough, means for sensing the flow velocity through the conduit, means for transmitting first and second bursts of acoustic energy axially through the conduit with a known time spacing therebetween, means for detecting doppler frequency shifted echo signals implicitly indicating the existence of bubbles moving with the fluid, means for establishing, based on the fluid flow velocity, a predetermined time interval following transmission of the second burst of energy during which an echo signal would occur if the implicit bubble were, fact real, and means for indicating the real existence of a bubble when an echo signal occurs in the predetermined time interval.

DETAILED DESCRIPTION

Figure 1:
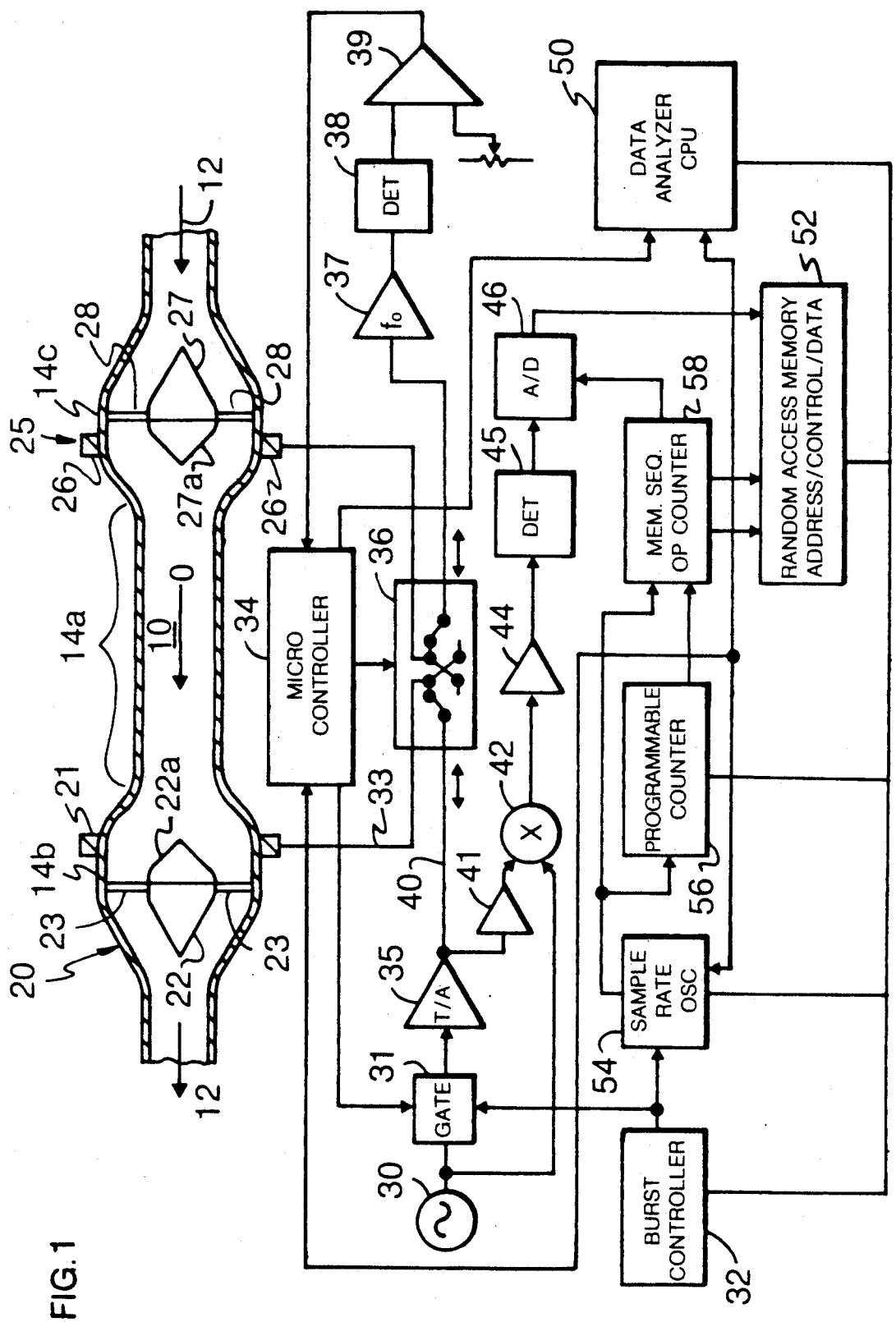
FIG. 1 is a schematic illustration of bubble detection apparatus of the present invention.

Referring to FIG. 1, the bubble detection system of the invention includes transducer assemblies 20 and 25 adapted to couple bursts of high frequency acoustic energy into a fluid 10 flowing in the direction of arrows 12 through an elongated conduit 14. Transducer assemblies 20,25 respectively include transducer rings 21,26 concentrically mounted around expanded sections 14b and 14c, of conduit 14. Deflectors 22 and 27 are mounted centrally within the expanded sections 14b and 14c by means of brackets 23 and 28. Each of the deflectors 22,27 are provided with 45° conical reflector surfaces 22a and 27a for deflecting acoustic energy from the transducers 90° directionally along a central conduit section 14a. The reflector surfaces 22a and 27a also serve to deflect acoustic energy emerging from the central conduit section 14a 90° to their respective transducer rings 21,26. Both transducer assemblies are used for measurement of flow velocity of fluid 10 through central conduit section 14a. Only one of the assemblies, specifically assembly 20 in the illustrated embodiment, is used in connection with the detection of reflected echo signal which would at least implicitly indicate the presence of bubbles in the conduit section 14a.

Pulsed sonic frequency signals used to produce the timed bursts of acoustic energy at transducer rings 21, 26 are provided by master oscillator 30 and gate circuit 31 operating under the control of a burst control circuit 32 and microcontroller 34. The pulses are fed by a transmitter amplifier circuit 35 and a reversing switch 36 to one or both of transducer rings 21 and 26 depending on whether fluid flow velocity measurement or bubble detection is involved, as determined by microcontroller 34. Timing of the transmitted bursts of acoustic energy is initiated by the burst controller 32 which comprises a scheduled interval timer. This timer also starts the sample rate oscillator 54 which controls the rate that random access memory (RAM) 52 is filled with digitized analog data from A/D converter 46. Programmable counter 56 counts the number of samples that are stored in RAM 52. When counter 56 reaches its programmed limit, it stops sample rate oscillator 54, thus halting any further memory storage, and interrupts master data analyzer CPU 50, informing it that the data acquisition is complete.

For fluid flow velocity measurement, acoustic pulses sensed by transducer rings 21,26 are fed by switch 36 to a signal detection stage including bandpass filter 37, detector circuit 38 and comparator circuit 39 to microcontroller 34. When fluid flow velocity is to be determined, microcontroller 34 actuates reversing switch 26 to cause a pair of successive acoustic energy pulses to be transmitted in opposite directions through central conduit section 14a. The start time and receive time of each of the pulses is provided by microcontroller 34 to data analyzer 50 which computes the transit time for each pulse and then computes the flow velocity in known manner from the difference in the two transit times.

Figure 2:
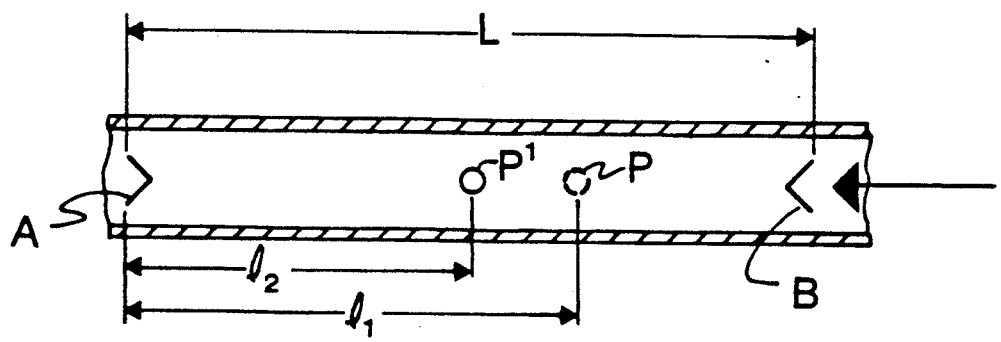
FIG. 2 is a bubble flow diagram useful in explaining the operation of the invention.

Referring to FIG. 2, the fluid velocity $V_F$ flowing right to left between transducers A and B is calculated from the expressions:

$$V_o + V_F = L/t_{BA} \quad (1)$$

and $$V_o - V_F = L/t_{AB} \quad (2)$$

where:
$V_o$ = acoustic velocity in a stationary fluid medium.
$t_{BA}$ = transit time of transmitted energy burst from transducer B to A.
$t_{AB}$ = transit time of transmitted energy burst from transducer A to B.
L = distance between transducer A and transducer B.

From the above expressions, it can be shown that the values of $V_o$ and $V_F$ are:

$$V_o = \frac{L}{2}\left(\frac{1}{t_{BA}} + \frac{1}{t_{AB}}\right) \quad (3)$$

and $$V_F = V_o\left(\frac{t_{AB} - t_{BA}}{t_{BA} + t_{AB}}\right) \quad (4)$$

Having thus determined the fluid velocity, it is then possible to use this value, given a predetermined time interval between transmitted acoustic bursts, to predict the time of occurrence of that a second and successive echoes would be returned from a real bubble moving in the fluid.

In the illustrated embodiment of FIG. 1, bubble detection is provided when an echo is sensed by transducer ring 21. By virtue of the movement of the bubble, the echo has a doppler frequency shift. The echo signal is sent via lines 33 and 40 through the left hand contacts of switch 36 to limiter amplifier 41 and then to mixer circuit 42 where it is mixed with signal frequency $f_o$ from oscillator 30 to generate sum and difference frequency components. The difference frequency component is passed through a low pass filter amplifier 44 and then to detector circuit 45 and an analog-to-digital converter circuit 46 where the detected signal is converted to digital form prior to being sent to random access memory 52. Implicitly, this detected echo signal might be presumed to be a result of a reflection from a bubble existing in central conduit section 14a. However, experience has shown that detection of single events such as this is not a reliable indicator of real occurrences of bubbles in the fluid. In accordance with a particular feature of the invention, when an echo signal occurs as just described, CPU 50 is programmed to calculate from the fluid flow velocity, previously determined as described above, a predetermined time interval following the initiation of a second pulse sent to transducer 21 during which an echo would be expected to be received if, in fact, the first echo signal was a true reflection from a bubble or particle. Thus, referring again to FIG. 2, during the bubble sensing interval, an echo at time $t_1$ from an implicit bubble p places the "bubble" at distance $l_1$ from the transmitting/receiving transducer A as determined by the relationship:

$$l_1 = \frac{V_o \cdot t_1}{2} \quad (5)$$

Assuming this is a real bubble moving at fluid velocity $V_F$, it can be predicted that the "bubble" would travel a distance $(l_1 - l_2)$ to position p' during a time interval of $t_n$ existing between successive transmitted acoustic energy bursts from the relationship:

$$V_F t_n = l_1 - l_2 \quad (6)$$

At the predicted new position p', therefore, the distance $l_2$ would be:

$$l_2 = \frac{V_o \cdot t_2}{2} \quad (7)$$

Combining equations (6) and (7) and solving for $t_2$ gives:

$$t_2 = \frac{2(l_1 - V_f t_n)}{V_o} \quad (8)$$

Thus knowing when a second echo would be received if the previous echo represented a true bubble, this time value can be set in data analyzer CPU 50 and memory 52 plus or minus some value such as 10% and, if the echo is sensed during this predetermined time interval, an indication can then be recorded to indicate the existence of an actual detected bubble.

In practice the predicted time interval is preferably determined with a finite duration e.g. plus or minus ten percent of the predicted time of arrival to account, for example, for slight differences between actual and calculated velocity of the fluid. Once CPU 50 establishes that a true detection of a bubble has occurred, CPU 50 can generate an output to an appropriate controller (not shown) in the fluid transport system indicating that a bubble has been detected along with its approximate size, so that suitable corrective action can be taken by the system. To further increase the reliability of real bubble detection, the predictive process can be repeated multiple times limited only by the length of the sensor conduit section.

In the simplest form of the invention, it can be assumed that the velocity profile of the fluid across the diameter of conduit section 14a is a constant. This would be the case if the fluid flow were an ideal turbulent flow. In many cases, however, fluid flows through the conduit with laminar flow wherein the fluid velocity varies parabolically as a function of the radial distance from the center of the conduit, the higher velocity occurring in the center. In such a case, fluid flow velocity would preferably be determined across the cross section of the conduit by known velocity measurement techniques. The CPU 50 would then be programmed to calculate a series of progressively different predicted time intervals as a function of radial distance from the center of the conduit during which a second echo would occur if, in fact, a real bubble were being detected. However, in this case, in order to further discriminate from an ambiguous detection, the CPU would preferably be programmed to analyze the returns from more than two transmitted signals, e.g. 6 or 8 successive samples in order verify the real existence of a bubble or particle by virtue of the repeated occurrence of an echo in the same one of the series of calculated time intervals corresponding to a given radius from the center of the conduit section 14a.

The invention has been described in detail with particular reference to a presently preferred embodiment, but it will be understood that variations and modifications can be effected within the spirit and scope of the invention.

What is claimed is:

1. An improved method for sensing the existence of a moving particle such as a bubble, in a fluid flowing through a section of an elongated conduit by means of acoustic echo sensing, the improvement comprising:
   sensing the velocity of the fluid flowing in the conduit section;
   transmitting a first acoustic signal along the conduit section and detecting an echo signal implicitly indicating the existence of a bubble in the conduit section;
   establishing on the basis of the known fluid velocity a predetermined time interval during which a second acoustic signal transmitted a known time after the first transmitted signal would produce a second echo signal if the implicit existence of the bubble is, in fact, real;
   transmitting the second acoustic signal along the conduit section at said known time after the first transmitted signal;
   and recording the real existence of the bubble only if a second echo is detected during the predetermined time interval.

2. The method of claim 1 further comprising
   sensing a nonuniform profile of fluid flow velocity across a cross sectional area of the fluid orthogonal to the direction of fluid flow through the conduit section;
   establishing a series of different predetermined time intervals corresponding to radial positions of the velocity flow from the center of the conduit section;
   and recording the real existence of a bubble detection only when an echo is detected in a given time interval series a predetermined minimum number of times in excess of twice.

3. The method of claim 1 further comprising: detecting doppler frequency shifted echo signals.

4. A system for sensing the existence of particles such as bubbles in a fluid flowing through a section of an elongated conduit comprising:
   means for determining the velocity of the fluid flowing in the conduit section;
   means for transmitting at least a pair of bursts of acoustic energy along the conduit section at predetermined time intervals between bursts;
   means for detecting echoes of said transmitted energy bursts implicitly reflected by a bubble in the conduit section;
   means responsive to detection of an echo from the first of the pair of transmitted bursts for establishing, from the known fluid velocity and the time interval between successive transmitted energy bursts, a predetermined time interval during which a second transmitted energy burst would produce a second echo detection if the implicit existence of the bubble is, in fact, real;
   and means for confirming the real existence of the bubble only if the second echo is detected during the predetermined time interval.

5. A system according to claim 4 wherein said fluid velocity determining means determines fluid velocity at a predetermined number of positions radially outward of the central axis of the conduit section to establish a velocity profile across a cross sectional area of the fluid orthogonal to the direction of fluid flow through the conduit section;
   said establishing means establishes a plurality of different time interval series corresponding to different radial positions of the velocity profile;
   and the confirming means includes means for recording the real existence of a detected bubble only when an echo is detected in a given time interval series a predetermined minimum number of times in excess of twice.

6. A system in accordance with claim 4 wherein said detecting means is adapted for detection of doppler frequency shifted echoes of said transmitted energy bursts.

* * * * *